United States Patent
Horn

(10) Patent No.: US 9,752,992 B2
(45) Date of Patent: Sep. 5, 2017

(54) VARIABLE IMAGE FIELD CURVATURE FOR OBJECT INSPECTION

(71) Applicant: KLA-Tencor Corporation, Milpitas, CA (US)

(72) Inventor: Paul Horn, Milpitas, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 308 days.

(21) Appl. No.: 14/662,602

(22) Filed: Mar. 19, 2015

(65) Prior Publication Data

US 2015/0276616 A1  Oct. 1, 2015

Related U.S. Application Data

(60) Provisional application No. 61/969,981, filed on Mar. 25, 2014.

(51) Int. Cl.
| | |
|---|---|
| *H04N 7/18* | (2006.01) |
| *G01N 21/88* | (2006.01) |
| *G01N 21/95* | (2006.01) |

(52) U.S. Cl.
CPC ..... *G01N 21/8851* (2013.01); *G01N 21/8806* (2013.01); *G01N 21/9501* (2013.01); *G01N 2201/06113* (2013.01); *G01N 2201/105* (2013.01)

(58) Field of Classification Search
CPC .......... G01N 21/9501; G01N 21/8806; G01N 21/8851; G01N 2201/105; G01N 2201/06113
USPC .......................................................... 348/87
See application file for complete search history.

(56) References Cited

U.S. PATENT DOCUMENTS

| | | |
|---|---|---|
| 4,231,636 A | 11/1980 | Abe |
| 6,777,166 B2 | 8/2004 | Weickenmeier |
| 7,126,668 B2 | 10/2006 | Smith et al. |
| 7,515,198 B2 | 4/2009 | Arimoto et al. |
| 7,671,979 B2 | 3/2010 | Smith et al. |
| 7,961,763 B2 | 6/2011 | Furman et al. |
| 2002/0167651 A1* | 11/2002 | Boonman ............... G03F 7/703 355/67 |
| 2004/0227916 A1* | 11/2004 | Kono ...................... G03F 7/703 355/53 |

(Continued)

FOREIGN PATENT DOCUMENTS

| | | | |
|---|---|---|---|
| JP | 362071834 A | * | 4/1987 |
| JP | 03-196009 A | * | 8/1991 |

(Continued)

OTHER PUBLICATIONS

Machine generated translation of JP 2007-294815 A to Furuya, Nov. 2007.*

*Primary Examiner* — David Harvey
(74) *Attorney, Agent, or Firm* — Hodgson Russ LLP

(57) ABSTRACT

Field curvature of an optical system is modified based on topography of the surface of a wafer such that an image of each of the segments of the surface is in focus across the segment. The wafer may be non-planar. The optical system may be a multi-element lens system connected to a controller that modifies the field curvature by changing position of the lens elements. The wafer may be held by a chuck, such as an edge grip chuck. Multiple optical systems may be arranged across a dimension of the wafer.

18 Claims, 9 Drawing Sheets

(56) References Cited

U.S. PATENT DOCUMENTS

| | | | |
|---|---|---|---|
| 2008/0021665 A1* | 1/2008 | Vaughnn | G01N 21/8851 702/84 |
| 2008/0084557 A1* | 4/2008 | Tan | G01N 21/8806 356/239.2 |
| 2008/0259297 A1* | 10/2008 | Kawakubo | G03F 7/70458 355/52 |
| 2008/0309927 A1 | 12/2008 | Grueneberg | |
| 2010/0110401 A1* | 5/2010 | Chung | G03F 7/70641 355/55 |
| 2010/0245810 A1 | 9/2010 | Hayashi et al. | |
| 2011/0205383 A1* | 8/2011 | Shah | H04N 5/232 348/222.1 |
| 2012/0015460 A1 | 1/2012 | Donaher | |
| 2012/0320257 A1 | 12/2012 | Shabtay et al. | |
| 2013/0089935 A1 | 4/2013 | Vukkadala et al. | |
| 2013/0235182 A1* | 9/2013 | Ono | H01J 37/28 348/80 |
| 2013/0279791 A1 | 10/2013 | Kaizerman et al. | |
| 2014/0340654 A1* | 11/2014 | Kuwata | G02B 13/16 353/69 |
| 2015/0233841 A1* | 8/2015 | Bobrov | H01L 22/12 356/237.5 |
| 2015/0276616 A1* | 10/2015 | Horn | G01N 21/8851 348/87 |
| 2017/0059972 A1* | 3/2017 | Ichimura | G03B 21/147 |

FOREIGN PATENT DOCUMENTS

| | | | |
|---|---|---|---|
| JP | 05094940 A | * | 4/1993 |
| JP | 2006-339574 | * | 12/2006 |
| JP | 2007-294815 A | * | 11/2007 |
| WO | 2012097163 A1 | | 7/2012 |

* cited by examiner

VARIABLE IMAGE FIELD CURVATURE FOR OBJECT INSPECTION

CROSS-REFERENCE TO RELATED APPLICATIONS

This application claims priority to U.S. provisional patent application No. 61/969,981 filed on Mar. 25, 2014, the disclosure of which is hereby incorporated by reference in its entirety.

FIELD OF THE DISCLOSURE

This disclosure relates to inspection of objects and, more particularly, to modifying field curvature during inspection of objects.

BACKGROUND OF THE DISCLOSURE

Wafers, such as semiconductor wafers, can become bowed. This renders the surface of the wafer curved (i.e., non-planar). For example, a point on the surface of a bowed wafer can deviate from a reference plane relative to a circumference of the surface. Such bowing may be a result of wafer processing or a result of stress or strain to the wafer. For example, layers or films on the wafer can cause stress or strain that leads to bowing. Bowing also may be a temporary effect due to, for example, chucking in wafer processing equipment.

Recently, edge grip chucks have increased in prevalence. Some manufacturers have sought to avoid using vacuum or electrostatic chucks when devices are formed on both flat surfaces of a wafer because the devices may contact the vacuum or electrostatic chuck and become damaged during chucking. Edge grip chucks avoid contact with most or all of the back side of a wafer by gripping the circumferential edge of the wafer. However, holding the wafer along its circumferential edge can lead to wafer sagging because the back side of the wafer is unsupported. This sagging can exacerbate bowing of the wafer due to stress or strain caused by the various layers or films formed on the wafer.

Inspection processes are routinely used during wafer processing to determine whether, for example, devices are being properly formed or whether defects exist on the wafer. Manufacturers may inspect wafers at multiple points during the manufacturing process. Early identification of defects can reduce manufacturing costs because time and resources are not spent processing a wafer with defects or non-functional devices. This inspection is typically done optically using an illumination source to project light on the wafer and a sensor to capture the reflected (brightfield) or scattered (darkfield) signal.

Inspection of a wafer surface is made challenging by process variations, such as wafer bowing. An optical system's ability to focus over the area of a surface is limited by its depth of field, or the axial depth of space on both sides of the focal plane within which objects appear acceptably sharp. In the case of wafer inspection, an image of devices on a wafer surface may be considered to have acceptably sharp focus when device defects can be resolved. When an optical system is focused on a portion or segment of the wafer, the wafer surface within the field of view of the optical system may not be in focus in its entirety. If a segment of the wafer surface in a field of view, or part of the wafer surface visible to the optical system at a particular position and orientation, is not within the depth of field of the optical system, portions of the image outside of the depth of field will not be in focus and, therefore, the optical system will not be able to produce a meaningful image of the wafer surface for purposes of inspection.

The ramifications of incomplete or improper inspection can be drastic. For example, while photoresist can be reworked if inspection determines the pattern to be incorrect, incomplete inspection may cause photoresist defects to go undetected. It may be impossible to make corrections once a wafer is etched or implanted. In that case, the wafer must be scrapped. As such, early detection of defects may allow for cost and time savings.

Previous methods of compensation for bowing during inspection, such as decreasing the imaging field of view (potentially requiring an increase in the number of sensors), are insufficient. Therefore, what is needed is a technique for inspection of bowed wafers. More particularly, what is needed is a system and method for inspection of bowed wafers that does not sacrifice sensitivity or throughput.

BRIEF SUMMARY OF THE DISCLOSURE

In a first embodiment, an inspection system is provided. The inspection system has an optical system and a controller. The optical system, which has lens elements, captures images of segments of a surface of a wafer. A position of the lens elements can be changed to modify field curvature. The controller is configured to receive topography data of the surface of the wafer and change a position of the lens elements based on the topography data of the surface of the wafer such that the field curvature of the optical system is modified and an image of each of the segments is in focus across the segment. A chuck, such as an edge grip chuck, may be configured to hold the wafer. A scanning system may be configured to move one of the wafer or the optical system with respect to each other. Additional optical systems may be arranged across a dimension of the wafer.

The inspection system may include a mapping system for generating the topography data of the surface that is operatively connected to the controller. The mapping system may include at least one laser configured to generate a laser beam that scans across the wafer.

The optical system may include a first lens element having a positive refractive power, a second lens element having a negative refractory power, and a third lens element having a positive refractory power. The first lens element, second lens element, and third lens element can include one or more lenses. The second lens element is adjacent to an imaging side of the first lens element. The third lens element is adjacent to an imaging side of the second lens element. The relative refractive powers of the first and second lens elements are such that optical ray traces from an object on the optical axis at infinity are approximately parallel with the optical axis in a space between the second and third lens elements. The first and second lens elements are movable relative to the third lens element for changing the field curvature of the optical system without varying a back focal distance of the optical system. An actuator in communication with the controller may be configured to change the position of the first lens element and/or the second lens element.

In a second embodiment, a non-transitory computer-readable storage medium is provided. The non-transitory computer-readable storage medium includes one or more programs for executing steps on one or more computing devices. These steps include receiving topography data of at least a segment of a surface of a wafer and modifying field curvature of an optical system based on the topography data such that an image of each of a plurality of segments of the surface is in focus across the segment. The steps also may include mapping the surface of a wafer to determine the topography data or moving one of the wafer or the optical system with respect to another of the wafer or the optical system.

In a third embodiment, an inspection method is provided. The inspection method includes receiving, at a controller, topography data of at least a segment of a surface of a wafer; modifying, based on the received topography data, field curvature of an optical system having a field of view corresponding to the segment; and capturing an image of the segment using the modified field curvature. The wafer may be held using a chuck, such as an edge grip chuck. One of the wafer or the optical system may be moved with respect to each other. The field curvature of an imaging lens of the optical system may be continually modified while the wafer is scanned. The inspection method can further include mapping the surface of the wafer to determine the topography data by scanning at least one laser beam across the surface.

DESCRIPTION OF THE DRAWINGS

For a fuller understanding of the nature and objects of the disclosure, reference should be made to the following detailed description taken in conjunction with the accompanying drawings, in which.

DETAILED DESCRIPTION OF THE DISCLOSURE

Figure 1:
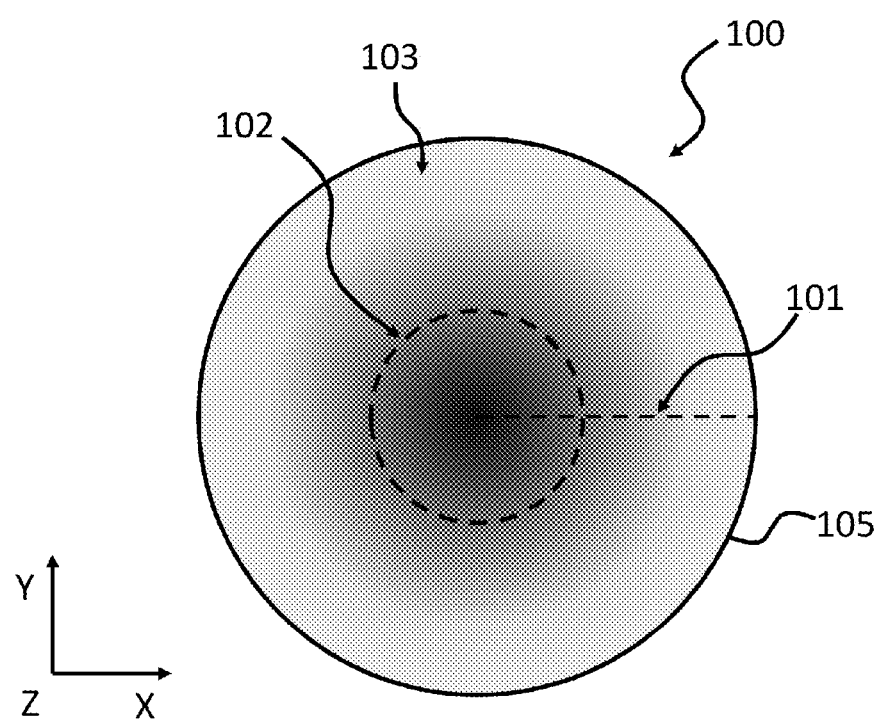
FIG. 1 illustrates a top surface of a wafer that is bowed.

Although claimed subject matter will be described in terms of certain embodiments, other embodiments, including embodiments that do not provide all of the benefits and features set forth herein, are also within the scope of this disclosure. Various structural, logical, process step, and electronic changes may be made without departing from the scope of the disclosure. Accordingly, the scope of the disclosure is defined only by reference to the appended claims.

The present disclosure provides a system and a computer-implemented method for imaging a wafer surface. Some embodiments of the disclosed system and method provide for identifying if non-planar regions exist within a wafer, identifying the extent of deviation of the individual segments from a designated plane, and, based on such identification, adjusting the field curvature of an optical system to accommodate the deviation for each individual segment so that an accurate image of the entire desired portion of the wafer surface is obtained. The position of lens elements can be changed to modify the field curvature. The system and a computer-implemented method for imaging a wafer surface disclosed herein can be used with an edge grip chuck holding a bowed wafer or with bowed wafers that cannot easily or otherwise be flattened using a chuck.

The initial identification of planar and/or non-planar regions of the wafer surface is obtained as a topography mapping output. This output may be a composite of several individual outputs from individual segments. One or more of the topography mapping outputs from individual segments or a composite from more than one segment is then inputted into a controller, which then directs the adjustment of the field curvature of an optical system by changing a position of lens elements in the optical system.

In one embodiment, the topography mapping output and the image are generated in the same pass of an inspection system over the wafer. In this embodiment, the topography mapping output for each segment of the wafer surface may be input into the controller, the field curvature of the optical system is modified based on the topography data for the segment, and an image is captured (imaging function) for that segment before the system moves to the next segment. In one embodiment, there may be a lag between the mapping function and the imaging function. For example, the imaging function may lag behind the mapping function by one or more segments.

In one embodiment, the topography mapping output and the image processing steps are carried out in separate passes. In this embodiment, the topography mapping output may be fed to the controller or may be stored on a storage medium for later inputting into the inspection system.

The results from any of the steps described herein may be stored on computer-readable storage medium and retrieved when needed. Such storage media are known to those skilled in the art. The results from the storage medium may be retrieved at a later time, so as to sync the mapping function with the imaging function, identify changes in the wafer topography as the wafer progresses through the manufacturing process, identify changes during use, etc.

FIG. 1 illustrates a top surface of an exemplary bowed wafer 100 for inspection by the presently disclosed system and method. As represented by the shading from the center to the circumferential edge 105 in FIG. 1, the circumferential edge 105 of the wafer 100 is a different height in the z-direction relative to the center of the wafer 100. Thus, the surface of the wafer 100 is not flat along the radial line 101. The difference in height between the center region of the wafer 100 (represented by the dashed circle 102) and the circumferential edge 105 may be approximately 100 µm or more in the z-direction. While the wafer 100 is bowl-shaped in FIG. 1, it should be noted that wafer bowing can be any deviation from a planar surface, including asymmetrical bowing, localized bowing, etc.

Due to bowing, portions of an image of the wafer 100 in FIG. 1 may not be in sharp enough focus (such as across a field of view of an optical system having a planar focal field) for meaningful device inspection. For example, if a depth of field of an optical system is less than approximately 20 µm and if the depth of field is set at the height of the wafer 100 surface at the circumferential edge 105 with a flat or planar field, then only region 103 (the portion of the wafer surface within the depth of field represented by hatching) will be in focus. Thus, images of the surface of the wafer 100 that are produced may not be sufficiently focused. For example, the image may not be focused enough across the entire image to determine whether photoresist is distorted, misaligned, has correct critical dimensions, or is free from surface irregularities.

The techniques of the present disclosure can be used to inspect wafers that are bowed, in part or in their entirety, where the bowing is greater than the depth of field of the optical system or where the bowing is within the depth of field. The techniques may also be used to inspect wafers that are not bowed at all. Further, the wafer may be a semiconductor wafer or may be a wafer of another type. The field curvature of the optical system can be adjusted to match or otherwise compensate for the bow of the wafer. Adjustment of the field curvature may be performed in real-time during inspection.

Figure 2:
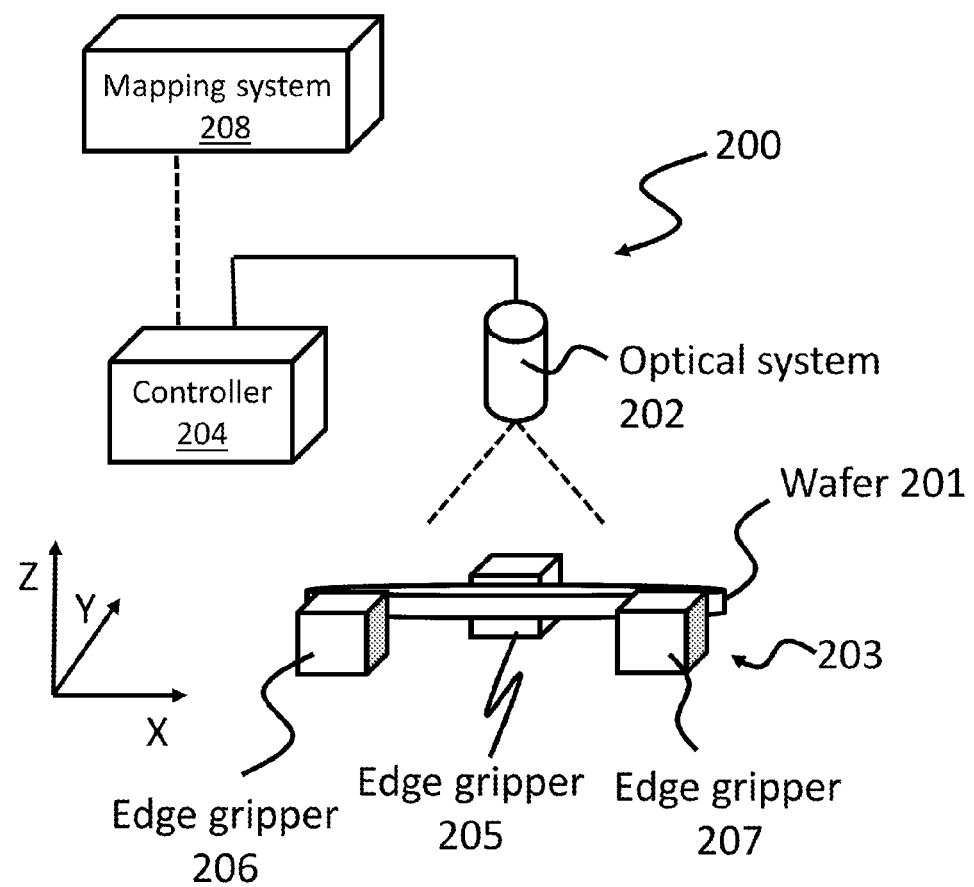
FIG. 2 is a perspective view of a system in accordance with an embodiment of the present disclosure.

An embodiment of an inspection system 200 of the present disclosure is shown in FIG. 2. The inspection system 200 includes an optical system 202 for capturing images of segments of a wafer surface. The optical system 202 is configured to be at a distance from the wafer 201 in the z-direction (where a wafer surface of a wafer 201 placed in the inspection system 200 is generally disposed in the x-y plane). The optical system 202 includes multiple lens elements capable of modifying field curvature as further described below. Embodiments of the optical system 202 may also include an illumination source and a sensor for capturing images of the surface of the wafer 201. The illumination source may be a laser, a light-emitting diode, a lamp, a laser-driven plasma source, or other sources. The illumination source can generate visible light or other wavelengths, and may be a broadband source or otherwise. The light may be polarized or non-polarized. Brightfield or darkfield illumination may be used. The optical system 202 can include one or more actuators, such as, for example, motors or servos, that enable adjustment of the position of the lens elements to affect focus and/or field curvature. The optical system 202 also can include other components, such as reflective elements, beam splitters, or additional lenses. The optical system 202 has an optical axis, or a central path along which light propagates through the optical system, defined by the lens elements of the optical system 202.

In one embodiment, the imaging system 202 has lens elements configured to change the field curvature. For example, the imaging system 202 can have three lens elements, where the first lens element has a positive refractive power, the second lens element has a negative refractory power, and the third lens element has a positive refractory power. The first and the second lens elements may move as a unit relative to the third lens element so that a change in the field curvature is effected. The first lens element and the second lens element are configured such that optical ray traces from an object at infinity are approximately parallel with the optical axis in a space formed between the second and the third lens elements. Such lens systems are known in the art. For example, see U.S. Pat. No. 4,231,636, which is incorporated herein by reference. The depth of field is related to at least the aperture and the focal distance, and, therefore, can be varied. In specific embodiments, the depth of field may be from 0.1 microns to 500 microns. The depth of field of the optical system 202 may be less than approximately 20 μm in one example. Other values for the depth of field are possible.

Figure 3:
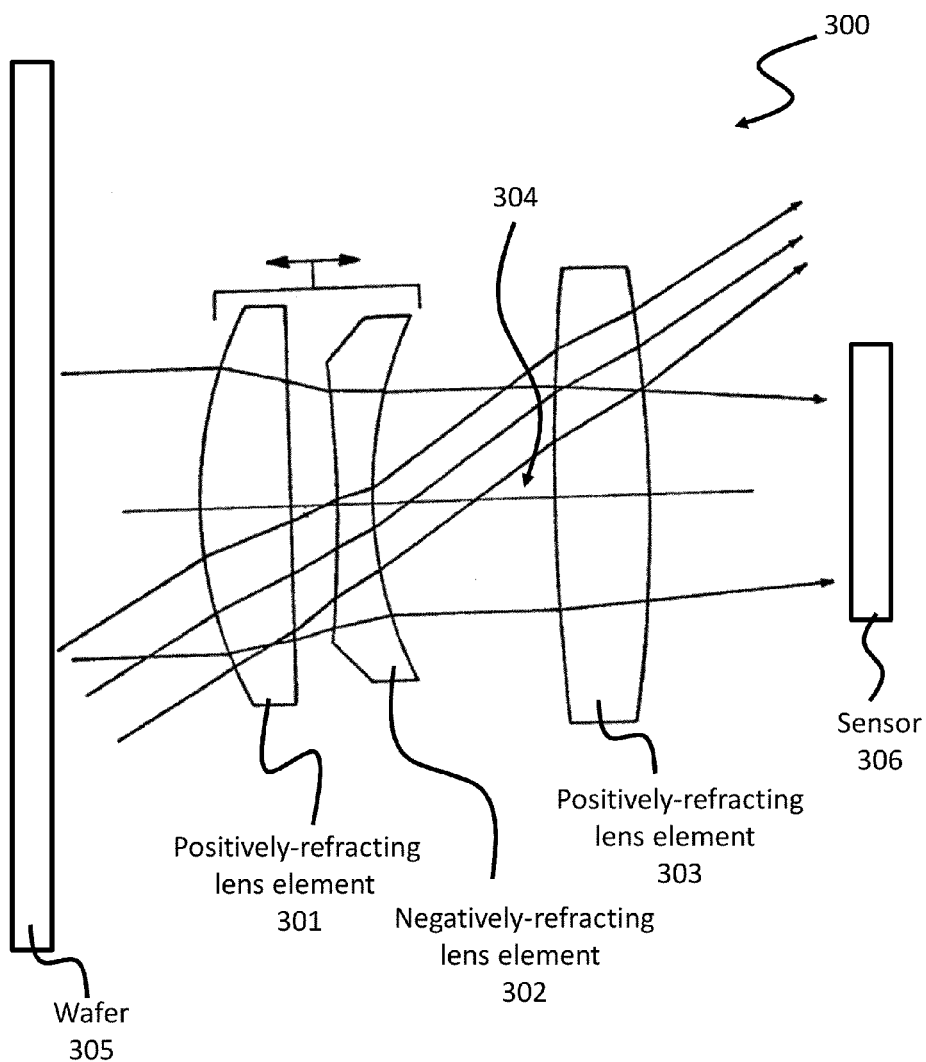
FIG. 3 is a block diagram representing an optical system in accordance with an embodiment of the present disclosure.

FIG. 3 is a block diagram representing an optical system 300 in accordance with the above-described embodiment of the present disclosure. The optical system 300 can be a variable field curvature lens system that enables variation of the field curvature independent of automatic compensation of the field curvature during focusing. Multiple lens elements may be used in the optical system 300. Each lens element can include one or more lenses. The optical system 300 contains a positively-refracting lens element 301 and a negatively-refracting lens element 302 that form a front lens group. The optical system 300 also contains a positively-refracting lens element 303. The front lens group shifts along the optical axis 304 to vary the field curvature as desired without shifting the point of intersection between the image plane and the optical axis 304. The relative positions of the first and second lens elements 301, 302 may be held constant during focusing and can be varied to permit introduction of variable field curvature. Focusing is enabled by relative movement of the positively-refracting lens element 301 to that of the remaining lenses in the optical system 300. Two of the movable lens elements, such as the first and second lens elements 301, 302, can have complimentary refractive powers or can move along the optical axis 304 as a single unit relative to a third lens element without varying the total back focal length of the lens system. A sensor 306 captures an image of the wafer 305.

Turning back to FIG. 2, the inspection system 200 further comprises a controller 204 configured to receive topography data of the surface of a wafer. The controller 204 is configured to change a position of lens elements in the optical system 202 based on the topography of the surface of the wafer 201 in order to modify the field curvature of the optical system 202 such that the surface of the wafer 201 in the field of view falls within the modified depth of field of the optical system 202. In this way, an image of a wafer surface segment captured using the optical system 202 is in focus (i.e., acceptably sharp focus) across the entirety of the wafer surface segment.

Based on the topography data, such as that received from optional mapping system 208, the controller 204 changes a position of the lens elements in the optical system 202 and modifies the field curvature of the optical system 202 to accommodate the topography of the surface of the wafer 201 (i.e., that portion of the surface of the wafer 201 within the field of view). In some embodiments, the controller 204 may use a look-up table to determine the required modifications of the field curvature. In other embodiments, the controller 204 may calculate the required modifications based on a pre-determined relationship between topography and field curvature. The controller 204 may be configured in other ways known in the art for such purposes.

The controller 204 also can control or manage image acquisition by the optical system 202 or movement of the optical system 202 or wafer 201 during scanning (further described below). In another embodiment, the controller 204 also can receive images or imaging data from the optical system 202.

It is to be appreciated that the controller 204 may be implemented in practice by any combination of hardware, software, and firmware. Also, its functions as described herein may be performed by one unit, or divided up among different components, each of which may be implemented in turn by any combination of hardware, software and firmware. Program code or instructions for the controller 204 to implement the various methods and functions described herein may be stored in controller readable storage media, such as a memory, within the controller 204, external to the controller 204, or combinations thereof.

Some embodiments of the presently disclosed system 200 may comprise a chuck 203 configured to hold a wafer 201. The chuck 203 may be an edge grip chuck similar to that illustrated in FIG. 2, but other chucks, such as electrostatic, vacuum, or other mechanical chucks, including chucks that contact or otherwise support the back side of the wafer 201, may be used. The edge grip chuck 203 uses three edge grippers 205-207 in the embodiment of FIG. 2, though other numbers of edge grippers are possible. In some embodiments, only the circumferential edge of the wafer 201 is gripped or otherwise contacted. The edge grippers 205-207 can be positioned outside the area of the wafer surface where device structures are located. The three edge grippers 205-207 in FIG. 2 are distributed along the circumference of the wafer 201. The use of three edge grippers 205-207 that hold the wafer 201 at its circumferential edge may minimize wafer distortions or sagging caused by the edge grippers 205-207. The locations of the edge grippers 205-207 also may be selected so as not to block imaging/inspection of the wafer 201.

In embodiments, two edge grippers or more than three edge grippers are used and spaced around the circumferential edge of the wafer 201. The edge grippers may be evenly spaced around the circumference of the wafer 201 or in other patterns. In some embodiments, the edge grip chuck is configured to interface with the entire circumference of the wafer 201.

The inspection system 200 may be configured to inspect the wafer 201 by scanning the wafer surface. For example, the optical system 202 may be used to capture a plurality of images of segments of the wafer surface as the wafer 201 and/or optical system 202 are moved relative to each other. This scanning function can be stepped or continuous. At least one of the wafer 201 and optical system 202 can move with respect to the other. In an embodiment, the optical system 202 is fixed and the wafer 201 moves. For example, the inspection system 200 may comprise a stage configured for motion in the x and/or y direction(s). The stage is configured to interface with the chuck 203 such that a wafer 201 can be scanned using the optical system 202. In another embodiment, the wafer 201 is fixed and the optical system 202 is configured to move. In yet another embodiment, both the wafer 201 and optical system 202 move with respect to the other.

In other embodiments, neither the optical system 202 nor the wafer 201 moves. Rather, the imaging function over the entire desired region of the wafer 201 is carried out by a single optical system configured to capture an image of the entire wafer surface or multiple optical systems each configured to capture an image of a portion of the wafer surface.

The scanning in inspection system 200 can be in any pattern. For example, this scanning may be in a serpentine pattern across the x-y plane. For example, the optical sensor 202 or wafer 201 may move in the x-direction to capture an image of a swath of the wafer surface, move in the y-direction to an adjacent swath, and then oppositely move in the x-direction over the surface of the wafer 201 to capture an image of the adjacent swath, thereby capturing a set of images representing the surface of the wafer 201 that is of interest. In another instance, a linear, zig-zag, or spiral pattern may be used. Each swath may include images or one or more segments.

For such scanning embodiments, the optical system 202 may comprise a sensor for capturing a plurality of images (i.e., samples) of at least a portion of the wafer surface. For example, the optical system 202 may comprise a line sensor made up of a one-dimensional array of imaging elements, wherein the line sensor is configured to sample images of the wafer 201 at a sampling frequency corresponding to the speed of the wafer 201 relative to the optical system 202 such that a continuous image of the wafer 201 is formed. A dimension (such as the width) of the formed image may correspond with a portion of the wafer 201 within a field of view of the optical system 202 during a scan. In such embodiments, the scanned portion of the wafer may be referred to as a swath. The line sensor may be charged-coupled device (CCD), a time delay and integration (TDI) sensor (effectively a line sensor), or other sensors known in the art. The line sensor may be configured to image a segment of any size. For example, the line sensor may be configured to image a segment having a size of 100 mm in one dimension. In this way, a 300 mm wafer may be inspected in a single pass beneath an inspection system having three optical systems as further described below.

In other embodiments, the optical system 202 comprises a 2-D imaging sensor configured to capture an image of a segment of the wafer 201. The size and shape of the segment may be defined by the configuration of the imaging sensor and/or an aperture along the optical path of the optical system 202. In such embodiments, the imaging sensor may be a CCD, a CMOS image sensor, or other sensors known in the art.

In one embodiment, a plurality of images may be needed to form an image of the entire desired portion of the wafer 201. A segment of an image may have a dimension from approximately 0.15 mm to larger than 100 mm.

While FIG. 2 illustrates inspection of a front side of the wafer 201, the inspection system 200 also can be configured for back side inspection of the wafer 201 or both front side and back side inspection of the wafer 201. In an embodiment, the optical system 202 is positioned relative to the wafer 201 to provide back side inspection. In another embodiment, multiple optical systems 202 are positioned relative to the wafer 201 to provide both front side and back side inspection of the wafer 201. The wafer 201 also may be flipped or otherwise rotated to provide both front side and back side inspection of the wafer 201.

Figure 4:
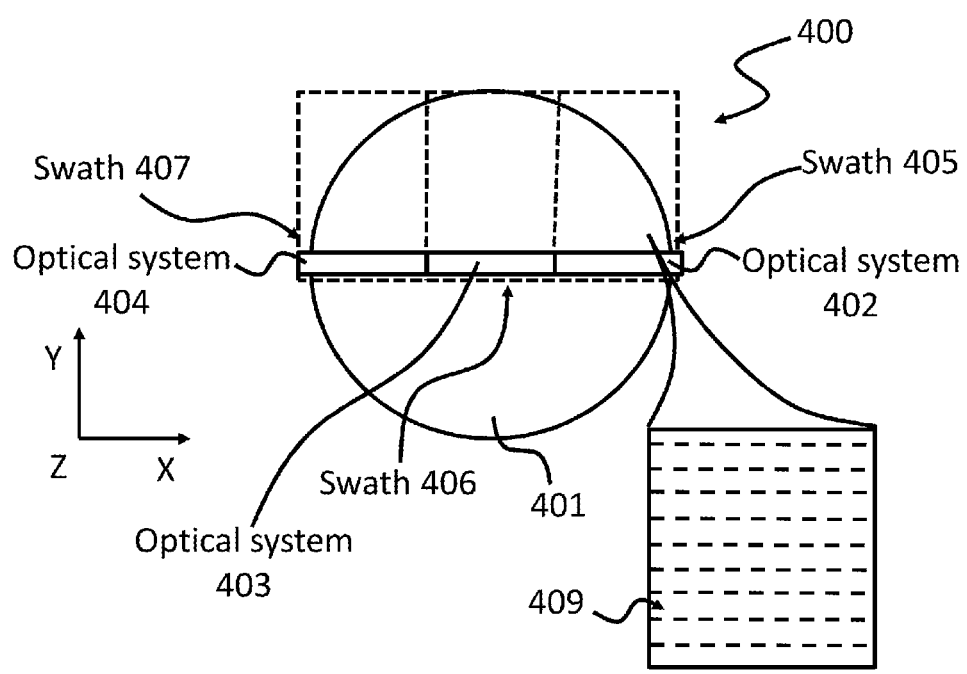
FIG. 4 is a top view of another system in accordance with another embodiment of the present disclosure.

FIG. 4 is a top view of another system 400 in accordance with another embodiment of the present disclosure. The system 400 includes optical systems 402-404. Each of the optical systems 402-404 may be the same as the optical system 202 of FIG. 2. Each of the optical systems 402-404 images a swath 405-407 (illustrated with dotted lines) on the wafer 401, which may be bowed. Each swath 405-407 may be approximately 100 mm in the x-direction in one example. For example, a 300 mm diameter wafer 401 uses three optical systems 402-404 that each produce images of swath that are 100 mm in the x-direction. Each swath 405-407 is made up of multiple segments 409, as seen in the inset with the dotted rectangles. Each of the segments 409 is imaged by an optical system during inspection. More or fewer segments 409 than illustrated in FIG. 4 may be used.

While each of the segments 409 are illustrated in FIG. 4 as being 100 mm in the x-direction, other shapes or dimensions are possible. For example, the segments may be squares. The size and shape of the segments can vary depending on the number of optical systems, type of optical system used, or type of sensor in the optical system.

Either the optical systems 402-404 or the wafer 401 moves with respect to the other in the embodiment of FIG. 4 during scanning. For example, movement may be enabled in the y-direction. In one particular embodiment, the wafer 401 moves in the y-direction while the optical systems 402-404 remain fixed. As the wafer 401 moves in the y-direction, the optical systems 402-404 image a segment in a swath, such as the swaths 405-407, on the surface of the wafer 402. The wafer 402 will move again and the optical systems 402-404 image a new segment on the surface of the wafer 402.

While the swaths 405-407 are illustrated as including multiple segments 409, the swaths 405-407 also can be a continuous image.

While three optical systems 402-404 are illustrated in FIG. 4, more or fewer optical systems may be used. A greater number of optical systems can enable smaller segments for imaging. A greater number of optical systems also could be configured to increase throughput by imaging more of the surface of the wafer 401 during each imaging step.

While not illustrated herein, the segments 409 or swaths 405-407 on the wafer surface can overlap.

The image of each of the segments 409 in FIG. 4 may be acceptable for inspection of the wafer surface despite the bowing of the wafer 401. The field curvature of the optical systems 402-404 can each be modified for a segment 409 depending on the topography of the wafer 401. This modification of field curvature can be individualized such that the field curvature of one or more of the optical systems 402-404 is different even in adjacent segments 409.

Figure 5:
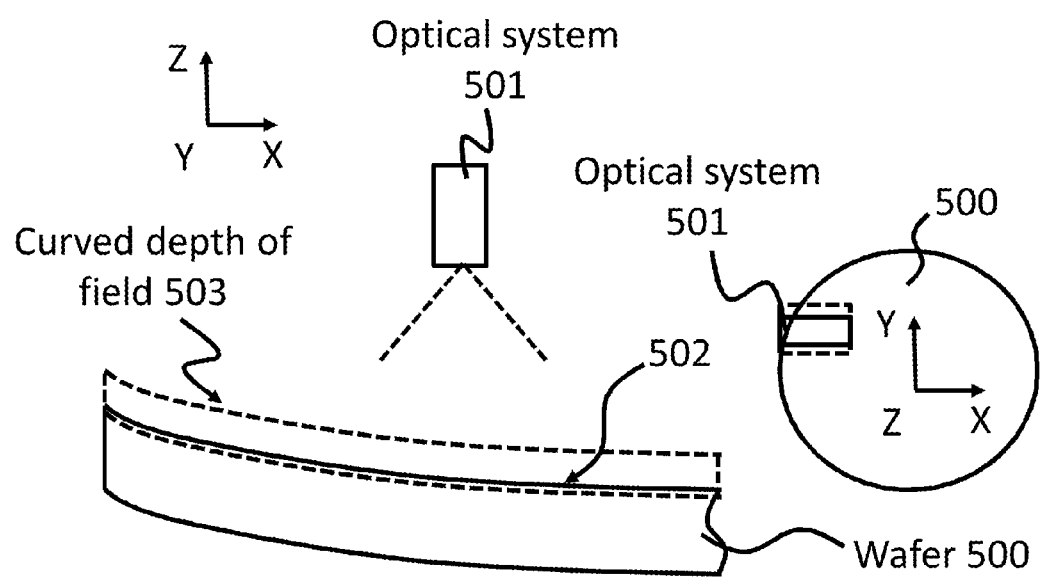
FIGS. 5-7 are cross-sectional views of a wafer that is bowed and field curvature with corresponding positions on the top surface of the wafer.
Figure 6:
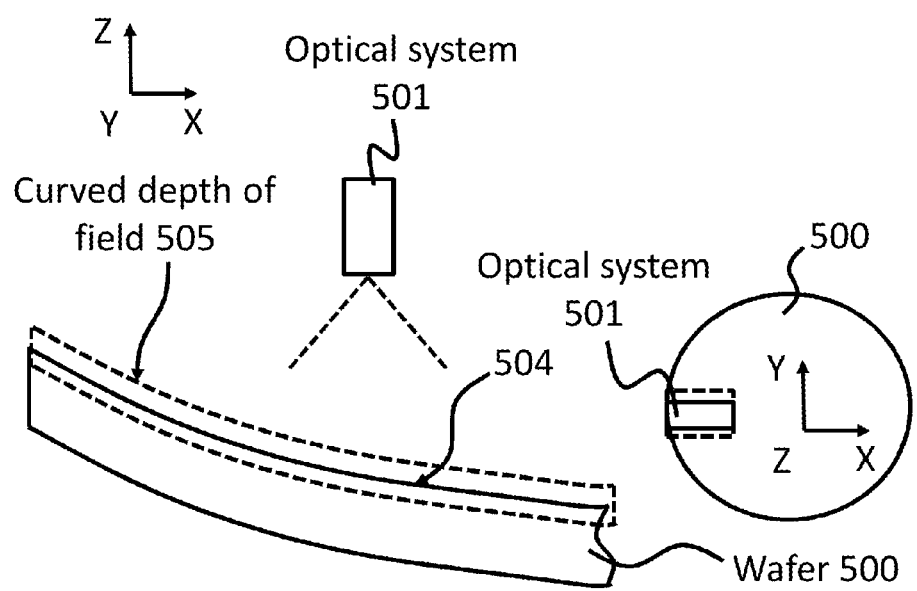
Figure 7:
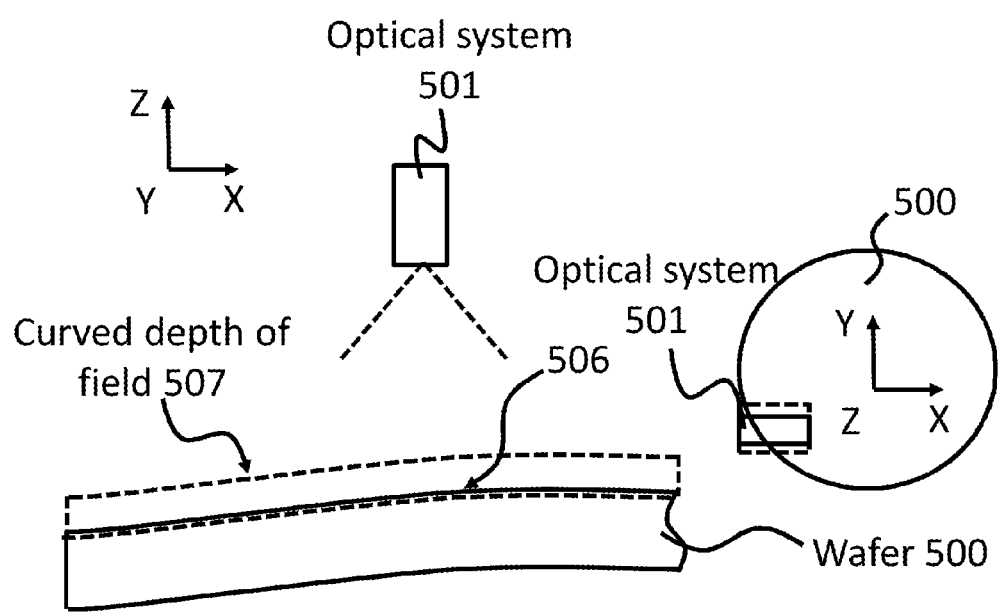

FIGS. 5-7 are cross-sectional views of a wafer 500 and field curvature with corresponding positions on the top surface of the wafer 500. The wafer 500 is at least partly bowed. As seen in each of FIGS. 5-7, a cross-sectional view of the wafer 500 in the x-z plane and a corresponding view of the surface of the wafer 500 in the x-y plane are illustrated.

In FIG. 5, a first segment on the surface of the wafer 500 in the x-y plane is illustrated. The surface topography 502 of this first segment is curved. The field curvature of the optical system 501 imaging the first segment is adjusted to have a curved depth of field 503 (outlined with a dotted line) by changing position of the lens elements in the optical system 501. As seen in FIG. 5, the surface topography 502 falls within the curved depth of field 503.

In FIG. 6, a second segment on the surface of the wafer 500 in the x-y plane is illustrated. The surface topography 504 in the second segment is curved and the curvature of the surface topography 504 is different from the surface topography 502. The field curvature of the optical system 501 imaging the second segment is adjusted to have a curved depth of field 505 (outlined with a dotted line) by changing position of the lens elements in the optical system 501. As seen in FIG. 6, the surface topography 504 falls within the curved depth of field 505.

In FIG. 7, a third segment on the surface of the wafer 500 in the x-y plane is illustrated. The surface topography 506 of the third segment is curved and the curvature of the surface topography 506 is different from the surface topography 504 or surface topography 502. The field curvature of the optical system 501 imaging the third segment is adjusted to have a curved depth of field 507 (outlined with a dotted line) by changing position of the lens elements in the optical system 501. As seen in FIG. 7, the surface topography 506 falls within the curved depth of field 507.

In each of FIGS. 5-7, the image produced by the optical system 501 may be in focus across the image of a segment. This is at least partly due to the curved depth of field produced by the optical system 501 and modifying the field curvature based on the surface topography of each segment by adjusting a position of the lens elements in the optical system 501. In an embodiment, the focus of the surface is achieved within $\pm\lambda/20NA^2$ where $\lambda$ is the mean wavelength of the optical system 501 and NA is the numerical aperture of the optical system 501.

A mapping system, such as the optional mapping system 208 in FIG. 2, can be used to generate data representing the topography of the wafer surface. Such a mapping system can be in communication with the controller, such as controller 204 in FIG. 2. In this way, the mapping system can transmit data containing the topography to the controller and the controller receives topography data from the mapping system. In another embodiment, the topography data from the mapping system is stored for later retrieval by the inspection system. The mapping system and the inspection system may be configured to establish common wafer coordinates such that the topography data of a wafer can be utilized to when inspecting the corresponding wafer. For example, the mapping system and/or the inspection system may be configured to establish wafer coordinates utilizing a laser beam as an edge finder. Other techniques for establishing wafer coordinates will be apparent in light of the present disclosure.

In some embodiments, the inspection system, such as the inspection system 200 in FIG. 2, comprises a topography mapping system and the controller receives topography data from the included mapping system. The topography mapping system and the optical system may be placed in the same housing or in a coupled housing to enable carrying out the mapping function and the imaging function in the same pass.

The mapping system can use one or more range finders to measure the relative deflection of the wafer surface in the z-direction. For the resulting image to be considered in focus, the topography of the wafer surface may be $<\pm\lambda/20NA^2$. For example, the one or more range finders may comprise range illumination source(s) such as, for example, lasers for mapping the topography of the wafer surface. In an embodiment, the topography of the wafer surface is measured using an array of laser beams that reflect from the surface of the wafer. For example, three laser beams may be used. The change in separation of the reflected laser beams and spatial translation of the array are measured to determine the topography. Intensity and orientation of the reflected laser beams can be an input in an algorithm to analyze curvature, tilt, or other topographical qualities of the wafer surface. Data can be provided in the form of a topographical map of the wafer surface.

Figure 8:
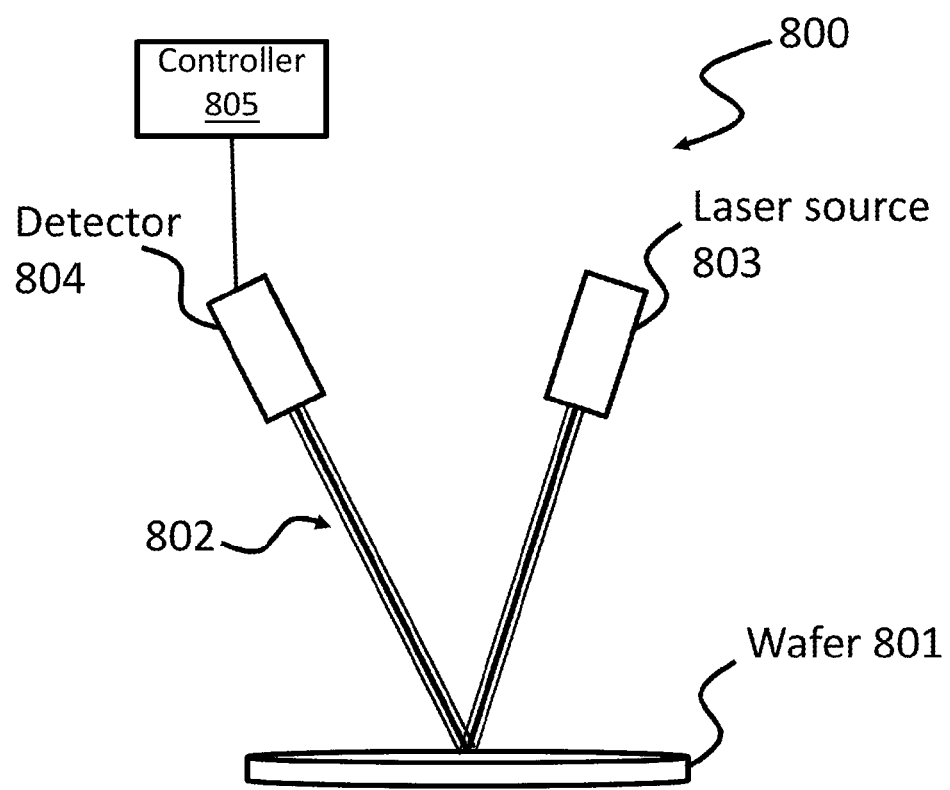
FIG. 8 is a block diagram of an embodiment of a mapping system.

In the embodiment of mapping system 800 illustrated in FIG. 8, the topography of the surface of the wafer 801 is measured using an array of three laser beams 802 generated by a laser source 803. The laser beams 802 can scan across the surface of the wafer 801. The reflected array of laser beams 802 is directed to a detector 804. Topography is determined using the laser beams 802 reflected from the surface of the wafer 801. A controller, such as the controller 805 that is connected with the detector 804, can determine topography based on the laser beams 802. The mapping system 800 may further include mirrors to align or reflect the laser beams 802.

The mapping system can use other methods known to those skilled in the art. For example, digital interpretation of microscopic images may be used to generate the topography of the wafer. In yet another example, an electronic sensor, such as a capacitance gauge, may be used to generate the topography of the wafer.

Figure 9:
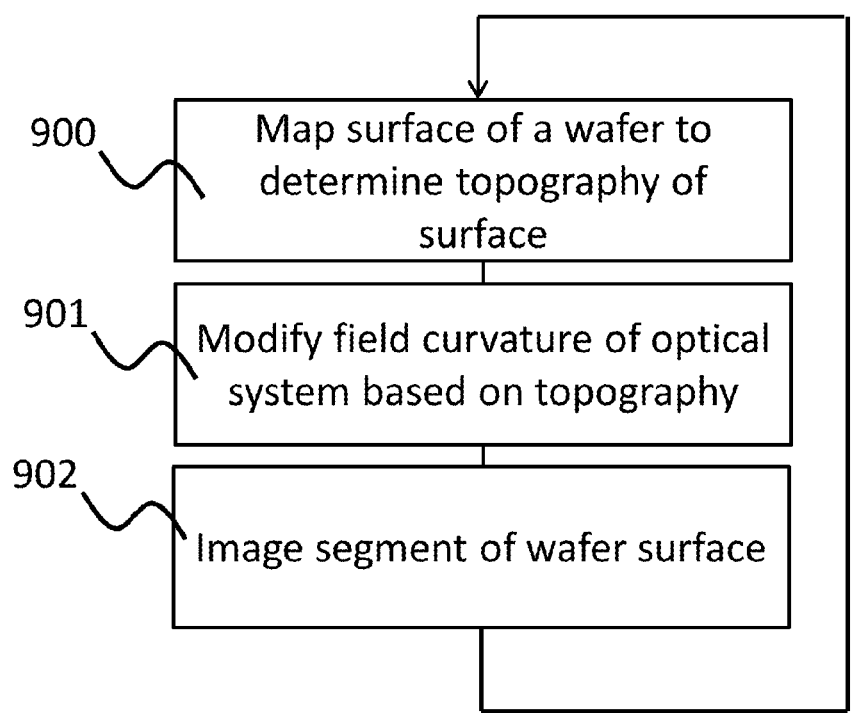
FIG. 9 is a flowchart of a method in accordance with an embodiment of the present disclosure.

An embodiment of the method of the present disclosure is illustrated in FIG. 9. A wafer surface is mapped to determine topography in 900. Some or all of the wafer surface may be non-planar. Field curvature of an optical system is modified based on the topography of the wafer surface in 901 and a segment of the wafer surface is imaged in 902. Field curvature may be modified by changing position of lens elements in the optical system. This process may be repeated for a different segment until a desired number of images are taken or a desired amount of the wafer surface has been imaged.

The method disclosed herein can be performed using a tangible medium. For example, a non-transitory computer-readable storage medium, comprising one or more programs, can be used to execute the method disclosed herein on one or more computing devices.

In an exemplary embodiment of an inspection system having a mapping system, the mapping system is configured such that topography data for a segment of a wafer is generated as the segment passes the mapping system. The mapping system is in electrical communication with the controller such that the controller receives the topography data for the segment. The controller utilizes the topography data to change a position of lens elements in an optical system to modify the field curvature of the optical system such that the optical system can be used to capture an acceptably-focused image of the segment when the segment is in the field of view of the optical system. As such, the controller of the inspection system is configured to coordinate use of the topography data for a segment with the image capture of the same segment. This process is repeated at a sample rate as the wafer is scanned by the inspection system. The controller timing may be such that the image capture lags the topography data by one or more segments. In other embodiments, the topography data is determined and the image is captured while the wafer is in substantially the same position relative to the optical system.

It should be noted that where a TDI sensor is utilized for image capture, the controller may change a position of the lens elements in an optical system to modify the field curvature and to accommodate the topography of multiple segments. As such, the change in topography between adjacent segments should be small enough such that each segment remains within the modified (curved) depth of field. Where the change in topography would prevent image capture of adjacent segments, the controller may be configured to truncate the number of sensor rows utilized in the TDI sensor, thereby sacrificing image brightness for image sharpness.

Irrespective of whether the topographical information is obtained in real-time or from storage, if the topographical information indicates an adjustment is needed for a segment (such as, because a displacement is noted in the z-direction), the controller directs the adjustment of field curvature of the optical system to accommodate for the displacement (if necessary). For example, the distance of the first and the second lens elements from the third lens element may be varied resulting in a change in field curvature. The optical system then moves on to the next segment and this process is repeated until the entire desired region of the wafer surface is scanned.

In one embodiment, the field curvature of an imaging lens of the optical system can be continually modified during scanning.

Generation of the topography data can be performed after chucking and before inspection begins. This may allow the topography data to include any wafer sagging in a chuck. The topography data may also be generated prior to chucking.

The image produced by the optical system may be pixelated. The pixel size of the resulting images may be on the scale of microns. For example, the pixel size may equal or correspond to 0.1 μm of the wafer and the degree of focus may be less than 1 μm. Other pixel sizes or degrees of focus are possible.

This adjustment of field curvature can be done in real-time as the optical system and wafer move with respect to one another during scanning. Higher inspection throughput can be achieved by using a smaller field of view for each segment thereby minimizing changes to the field curvature. Higher throughput may also be achieved by minimizing the number of segments needed to inspect the surface of the wafer.

The system and method described herein may be used for inspection of any type of wafer. For example, the wafer may be a semiconductor wafer or another type of wafer, such as those used to manufacture LEDs, solar cells, magnetic discs, flat panels, or polished plates. Other objects also may be inspected, as is known to those skilled in the art. Embodiments of the present disclosure can be configured to inspect wafers that may be generally circular, generally rectangular, or other shapes. For example, the wafer may be a generally circular semiconductor wafer. Embodiments may be configured to inspect wafers of different sizes. In some embodiments, the wafer may have a diameter such as 100 mm, 200 mm, 300 mm, or 450 mm and a thickness from approximately 500 μm to 1,000 μm. In other examples, the wafer may be a generally rectangular solar cell that has dimensions from approximately 100 mm to 200 mm square and a thickness from approximately 150 μm to 300 μm. In another example, the system and method described herein may be used to inspect semiconductor photomasks.

Bowing across a wafer is typically smooth with low frequency irregularities. The bowed wafer may have a substantially bowl-like shape. However, bowing also can be irregular due to wafer processing, layers on the wafer, or films on the wafer that cause stress or strain in particular regions. Embodiments of the present disclosure, regardless of sensor type, can be configured to adequately inspect a wafer even with irregular bowing.

Although the present disclosure has been described with respect to one or more particular embodiments, it will be understood that other embodiments of the present disclosure may be made without departing from the scope of the present disclosure. Hence, the present disclosure is deemed limited only by the appended claims and the reasonable interpretation thereof.

What is claimed is:

1. An inspection system comprising:
    an optical system for capturing images of segments of a surface of a wafer, the optical system having lens elements, wherein a position of the lens elements can be changed to modify field curvature, wherein the lens elements include:
        a first lens element having a positive refractive power, the first lens element comprising one or more lenses;
        a second lens element having a negative refractory power, the second lens element being adjacent to an imaging side of the first lens element, and the second lens element comprising one or more lenses; and
        a third lens element having a positive refractory power, the third lens element being adjacent to an imaging side of the second lens element, and the third lens element comprising one or more lenses; and
    a controller configured to:
        receive topography data of the surface of the wafer; and
        change a position of at least one of the lens elements based on the topography data of the surface of the wafer such that the field curvature of the optical system is modified and an image of each of the segments is in focus across the segment.

2. The inspection system of claim 1, further comprising a mapping system for generating the topography data of the surface, wherein the mapping system includes a laser source configured to generate a laser beam and a detector configured to receive the laser beam, and wherein the mapping system is operatively connected to the controller.

3. The inspection system of claim 2, wherein the laser beam is configured to scan across the wafer.

4. The inspection system of claim 1, wherein the relative refractive powers of the first and second lens elements are such that optical ray traces from an object on the optical axis at infinity are approximately parallel with the optical axis in a space between the second and third lens elements, and the first and second lens elements are movable relative to the third lens element for changing the field curvature of the optical system without varying a back focal distance of the optical system.

5. The inspection system of claim 1, further comprising an actuator in communication with the controller, the actuator configured to change the position of the first lens element and/or the second lens element.

6. The inspection system of claim 1, further comprising additional optical systems arranged across a dimension of the wafer.

7. The inspection system of claim 1, further comprising a chuck configured to hold the wafer.

8. The inspection system of claim 7, wherein the chuck comprises an edge grip chuck.

9. The inspection system of claim 1, further comprising a scanning system configured to move one of the wafer or the optical system with respect to each other.

10. A non-transitory computer-readable storage medium, comprising one or more programs for executing the following steps on one or more computing devices:
receiving topography data of at least a segment of a surface of a wafer; and
modifying field curvature of an optical system based on the topography data such that an image of each of a plurality of segments of the surface is in focus across the segment wherein the optical system comprises a first lens element having a positive refractive power, a second lens element having a negative refractory power, and a third lens element having a positive refractory power, wherein the first lens element comprises one or more lenses, wherein the second lens element is adjacent to an imaging side of the first lens element, wherein the second lens element comprises one or more lenses, wherein the third lens element is adjacent to an imaging side of the second lens element, and wherein the third lens element comprises one or more lenses.

11. The non-transitory computer-readable storage medium of claim 10, further comprising mapping the surface of a wafer to determine the topography data.

12. The non-transitory computer-readable storage medium of claim 10, further comprising moving one of the wafer or the optical system with respect to another of the wafer or the optical system.

13. An inspection method comprising:
receiving, at a controller, topography data of at least a segment of a surface of a wafer;
modifying, based on the received topography data, field curvature of an optical system having a field of view corresponding to the segment, wherein the optical system comprises a first lens element having a positive refractive power, a second lens element having a negative refractory power, and a third lens element having a positive refractory power, wherein the first lens element comprises one or more lenses, wherein the second lens element is adjacent to an imaging side of the first lens element, wherein the second lens element comprises one or more lenses, wherein the third lens element is adjacent to an imaging side of the second lens element, and wherein the third lens element comprises one or more lenses; and
capturing an image of the segment using the modified field curvature.

14. The inspection method of claim 13, further comprising mapping the surface of the wafer to determine the topography data by scanning at least one laser beam across the surface.

15. The inspection method of claim 13, wherein the field curvature of an imaging lens of the optical system is continually modified while the wafer is scanned.

16. The inspection method of claim 13, further comprising moving one of the wafer or the optical system with respect to each other.

17. The inspection method of claim 13, further comprising holding the wafer using a chuck.

18. The inspection method of claim 17, wherein the chuck is an edge grip chuck.

* * * * *